United States Patent
DeYoe et al.

(10) Patent No.: US 7,469,159 B2
(45) Date of Patent: Dec. 23, 2008

(54) METHOD FOR MEASURING NEUROVASCULAR UNCOUPLING IN FMRI

(75) Inventors: Edgar DeYoe, Delafield, WI (US); John L. Ulmer, Brookfield, WI (US)

(73) Assignee: The MCW Research Foundation, Inc., Milwaukee, WI (US)

( * ) Notice: Subject to any disclaimer, the term of this patent is extended or adjusted under 35 U.S.C. 154(b) by 485 days.

(21) Appl. No.: 11/138,509

(22) Filed: May 26, 2005

(65) Prior Publication Data

US 2007/0010732 A1  Jan. 11, 2007

(51) Int. Cl.
*A61B 5/05* (2006.01)
*G06K 9/00* (2006.01)

(52) U.S. Cl. .................. 600/411; 600/410; 600/558; 382/128

(58) Field of Classification Search .......... 600/410, 600/411, 554, 558, 559, 555, 587, 595; 351/224; 382/128

See application file for complete search history.

(56) References Cited

U.S. PATENT DOCUMENTS

| | | | |
|---|---|---|---|
| 5,459,536 A | 10/1995 | Shalon et al. | |
| 6,260,021 B1 | 7/2001 | Wong et al. | |
| 6,430,431 B1 * | 8/2002 | DeYoe | 600/410 |
| 6,527,391 B1 | 3/2003 | Heijl et al. | |

OTHER PUBLICATIONS

Hirsch et al., An Integrated Functional Magnetic Resonance Imaging Procedure for Preoperative Mapping of Cortical Areas Associated with Tactile, Motor, Language, and Visual Functions, Neurosurgery, vol. 47, No. 3, Sep. 2000, pp. 711-722.*

John L Ulmer et al, Lesion-Induced Pseudo-Dominance at Functional Magentic Resonance Imaging: Implications for Preoperative Assessments, Neurosurgery, vol. 55, No. 3, Sep. 2004, pp. 569-581.

Andrei I. Holodny, et al, The Effect Of Brain Tumors On BOLD Functional MR Imaging Activation In The Adjacent Motor Cortex: Implications For Image-guided Neurosurgery, AJNR AM J Neuroradiol 21:1415-1422, Sep. 2000.

Young-Jun Lee et al, The Role Of Functional MR Imaging In Patients With Ischemia In The Visual Cortex, AJNR Am J Neuroradiol 22:1043-1049, Jun./Jul. 2001.

Stephane Lehericy et al, Arteriovenous Brain Malformation: Is Functional MR Imaging Reliable For Study Language Reorganization In Patient? Initial Observations, Radiology, vol. 223, No. 3, Jun. 2002, pp. 672-682.

Axel Schreiber et al, The Influence Of Gliomas and Nonglial Space-Occupying Lesins On Blood-Oxygen-Level-Dependent Contrast Enhancement, AJNR Am J Neuroradiol 21:1055-1063, Jun./Jul. 2000.

John L. Ulmer et al, Pseudo-Reorganization Of Language Cortical Function At fMR Imaging: A Consequence of Tumor-Induced Neurovascular Uncoupling, AJNR Am J Neuroradiol 24:213-217, Feb. 2003.

* cited by examiner

*Primary Examiner*—Eric F Winakur
*Assistant Examiner*—Katherine L Fernandez
(74) *Attorney, Agent, or Firm*—Quarles & Brady LLP

(57) ABSTRACT

Neurovascular uncoupling that causes fMRI data to underestimate viable neuronal activity in the brain is detected and indicated to assist in pre-surgical planning. Tasks associated with the cortical region in question are performed while the fMRI measurement of brain activity is measured and the same tasks are performed while task performance is measured directly. Neurovascular uncoupling is detected and indicated by comparing the results of fMRI measurement and direct measurement.

9 Claims, 7 Drawing Sheets

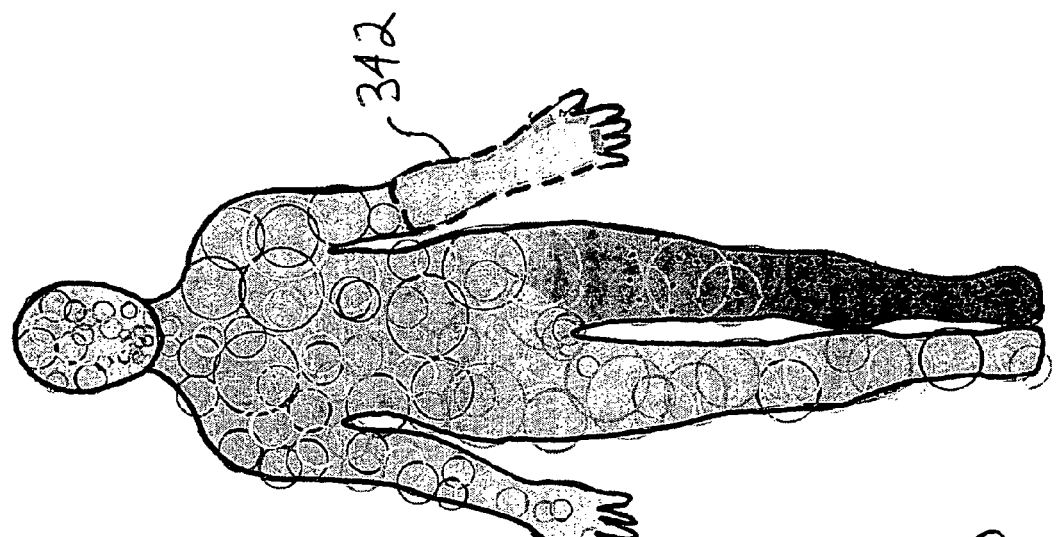
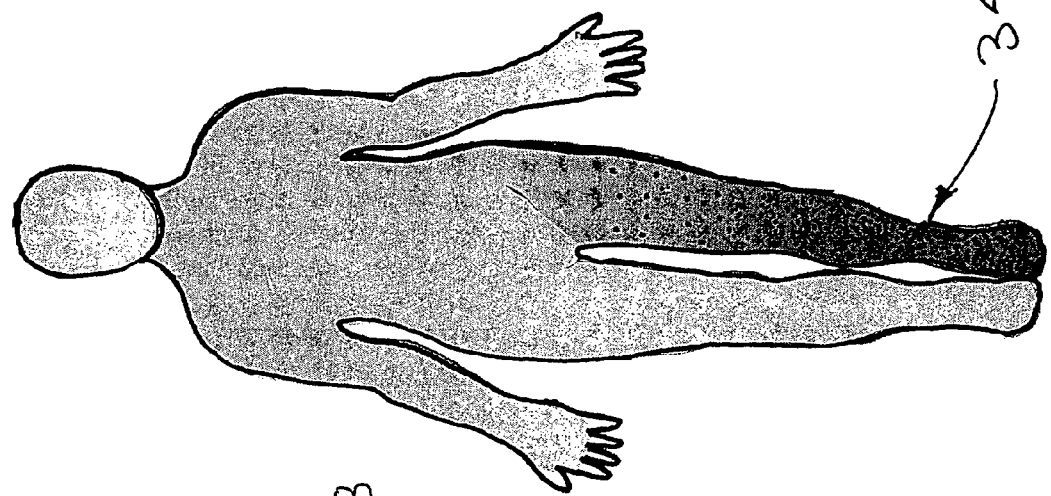
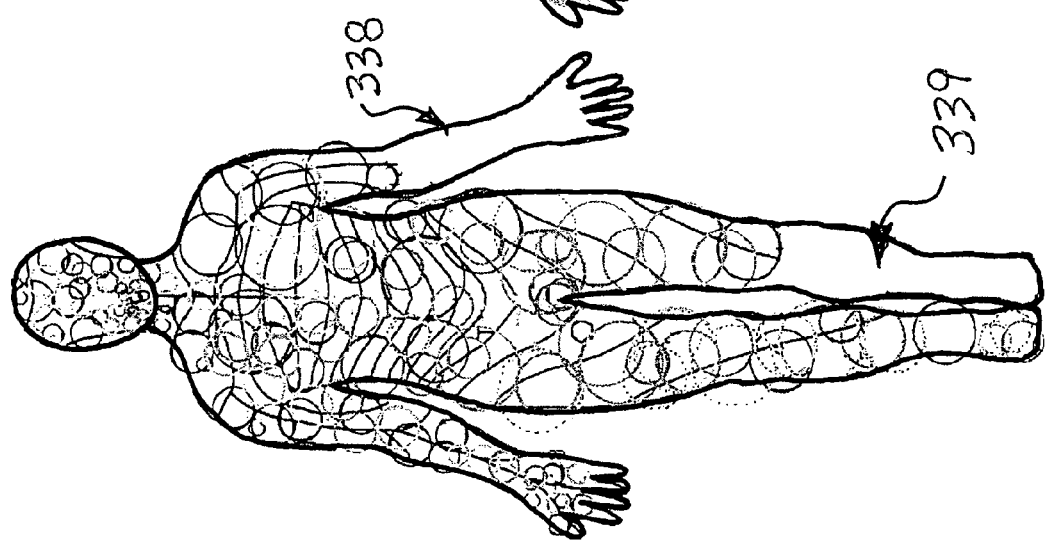

METHOD FOR MEASURING NEUROVASCULAR UNCOUPLING IN FMRI

STATEMENT REGARDING FEDERALLY SPONSORED RESEARCH

This invention was made with government support under Grant Nos. NS52725 and EY13801 awarded by the National Institute of Health. The United States Government has certain rights in this invention.

BACKGROUND OF THE INVENTION

The field of the invention is functional magnetic resonance imaging (fMRI) techniques, and in particular, the use of fMRI images for surgical planning.

Functional magnetic resonance imaging (fMRI) technology provides a new approach to study neuronal activity. Conventional fMRI detects changes in cerebral blood volume, flow, and oxygenation that locally occur in association with increased neuronal activity induced by functional paradigms. As described in U.S. Pat. No. 5,603,322, an MRI system is used to acquire signals from the brain over a period of time. As the brain performs a task, these signals are modulated synchronously with task performance to reveal which regions of the brain are involved in performing the task. Much research has been done to find tasks which can be performed by patients, and which reveal in an fMRI image acquired at the same time, regions in the brain that function in response to the tasks.

Functional magnetic resonance imaging (fMRI) has been used extensively to study normal brain function, psychiatric conditions, learning disabilities, neurodegenerative conditions, recovery from stroke, and the relationship of eloquent cortex to brain tumors and arteriovenous malformations (AVMs). The pre-operative use of fMRI to identify eloquent cortex near resectable lesions is becoming a common clinical imaging scenario. Mapping eloquent cortex with fMRI relies on blood oxygen level dependent (BOLD) contrast. The physiological basis of BOLD signal is the regional vasoactive response induced by neuronal activity, causing increases in regional cerebral blood flow (rCBF), blood oxygen concentration, and consequently, fMRI signal. Yet, it is clear that BOLD contrast can be significantly compromised adjacent to regional cerebral pathology. For example, cortical BOLD signal can be reduced by the presence of glial tumors, both at the edge of the tumor and in vascular territories somewhat removed from the tumor. Loss of regional cerebral vasoactivity near lesions is thought to be a major contributing factor. When using BOLD fMRI, such effects may result in the underestimation of genuine neuronal function and may therefore cause an under-appreciation of the location of functioning cortical neurons near operable lesions. The result could be unexpected post-surgical neurological deficits.

Lesion-induced neurovascular uncoupling may also adversely affect assessments of cerebral dominance for certain key functions such as speech and language comprehension, movement control, and other cognitive abilities. It is common to assume that a greater extent and/or magnitude of cortical activation in one hemisphere of the brain are indicative of functional dominance in that hemisphere and that the opposite hemisphere may be subjected to more aggressive surgical resection with little risk. If, under pathological conditions, normal or near normal function is maintained but fMRI shows a shift in relative hemispheric activation away from the lesion, then it might be assumed that the function of the affected cortex has been taken over by the homologous area in the unimpaired hemisphere. Indeed, fMRI data showing a lesion-induced shift in relative cortical activation have been taken as evidence for cortical reorganization. However, this premise can be erroneous if, under certain conditions, the BOLD mechanism rather than neuronal function is selectively impaired.

Thus, the consequences of lesion-induced neurovascular uncoupling are to decrease the accuracy of BOLD fMRI information by underestimating genuine cortical neuronal function and by falsely implying cortical reorganization. The effects of this phenomenon on the process of pre-surgical planning and on the subsequent outcome of surgery are potentially catastrophic.

SUMMARY OF THE INVENTION

Our invention provides a solution to this problem, by providing a method of identifying neurovascular uncoupling and mapping brain areas of under-represented neuronal function. The method entails a comparison of a functional field map generated from BOLD fMRI data to a behavioral field map or similar assessment tool of a given neuronal functional system. Mismatches between the fMRI functional field map and a behavioral field map can identify brain regions where neuronal function is preserved but fMRI signals are absent, thereby identifying potential neurovascular uncoupling.

We have developed a technique for direct comparison between behavioral visual field testing and visual fMRI functional field (FF) mapping, as an indicator of neurovascular coupling in the visual cortex. The technique relies on the retinotopic arrangement of the visual cortex, where each point in the visual field has a corresponding cortical processing location in the occipital lobe. FF Mapping is a technique described in U.S. Pat. No. 6,430,431 that displays the precise spatial correlation of a locus in the subject's visual field to a sub-region of visual cortex in the subject's brain responsible for processing that visual information. By directly comparing the FF Map to a behavioral visual field map, such as the Humphrey and Goldman perimetry map, we identify sub-regions of visual cortex where genuine neuronal function is not reflected in a normal BOLD response. FFMap-behavioral field mismatch areas are identified by a lack of activation, a reduction in activation area compared to analogous regions of the normal hemisphere, or a significant decline in correlation coefficients in activated cortex compared to the normal hemisphere. Sub-regions showing a FFMap-behavioral response mismatch with altered signal amplitude, temporal phase, or both compared to the normal corresponding contralateral visual cortex indicate the presence of pathologically induced BOLD-neuronal uncoupling.

This approach can be extended to other sensory modalities. For the somato-sensory system, the comparison is between a tactile functional field map generated by fMRI data and a behavioral map generated by sensory stimulation reported by the patient. This is done by electrically stimulating different areas of the skin surface in a systematic fashion to create an fMRI neuronal functional field map of those skin surfaces. This sensory neuronal functional field map can, subsequently be compared to the observed sensation of electrical stimulation of those skin areas by a patient. A response button is used to cue every time that he or she felt stimulation from the electrode in a known skin area. Again, a mismatch between these two maps indicates a region of neurovascular uncoupling in which the sensory system is not represented by BOLD fMRI neuronal measurement. A similar method may be employed for passive stimulation of the motor system, and an adaptation may be used to test the reliability of BOLD fMRI neuronal measurements for components of the language system as well.

An object of the present invention is to indicate the quality of fMRI neuronal measurement data on a patient-by-patient basis and detect the presence of neurovascular uncoupling.

Another object of the invention is to indicate the quality of fMRI data for each functional brain system tested and confirm that all functional areas tested are, in fact, represented by BOLD fMRI activation.

These objectives are achieved by comparing functional maps generated by BOLD fMRI measurements with corresponding behavioral maps obtained from the patient's response to sensory stimulation. This comparison is performed computationally through a computer process that is coupled to a visual display. Detection of a fMRI functional map-behavioral map mismatch operates automatically and provides a warning to the physician that neurovascular uncoupling is present and an under-representation of actual brain function by the BOLD fMRI measurements has occurred. The display also provides a brain map of the extent of sensory or motor stimulation that has been under-represented by the BOLD fMRI data. The end result is an automatic method of quality assurance of BOLD fMRI neuronal measurements on a patient-by-patient basis.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 9A is a functional field map produced using another preferred embodiment of the invention;

FIG. 9B is a sensory field map used with the functional field map of FIG. 9A to practice another preferred embodiment of the invention; and FIG. 9C is an overlay of the field maps of FIGS. 9A and 9B.

DETAILED DESCRIPTION OF THE PREFERRED EMBODIMENT

Figure 1:
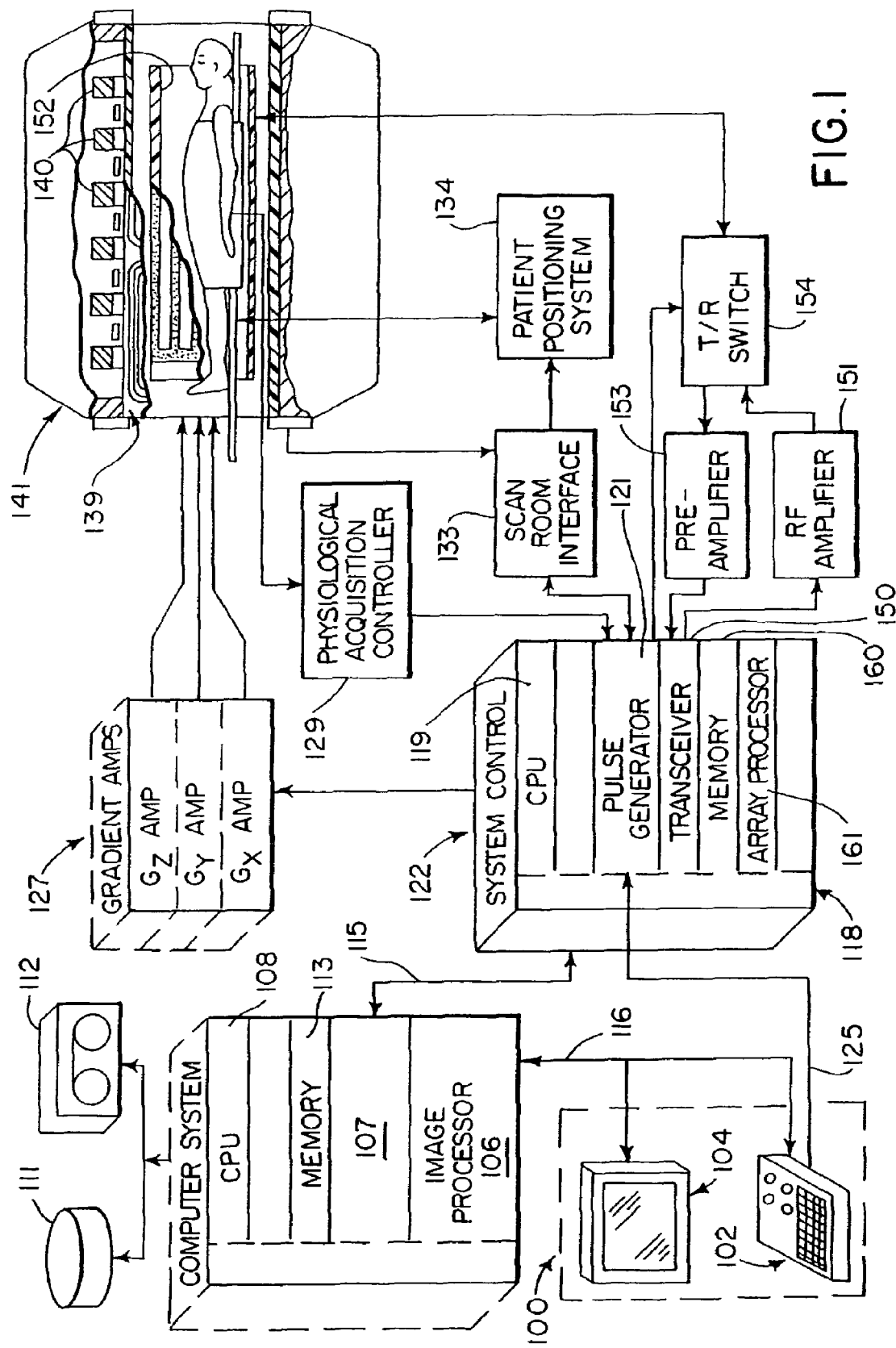
FIG. 1 is a block diagram of an MRI system used to acquire fMRI images according to the present invention.

Referring first to FIG. 1, there is shown the major components of a preferred NMR system which incorporates the present invention and which is sold by the General Electric Company under the trademark "SIGNA". The operation of the system is controlled from an operator console 100 which includes a keyboard 102 and a plasma display/touch screen 104. The console 100 communicates through a communications link 116 with a separate computer system 107. Through the keyboard 102 and controls 103, an operator controls the production and display of images by an image processor 106 in the computer system 107.

The computer system 107 is formed about a backplane bus and it includes a number of modules which communicate with each other through this backplane. These include a CPU module 108 that controls the backplane, and a module that connects the computer system 107 to a set of peripheral devices, including disk storage 111 and tape drive 112. The computer system 107 also includes a memory module 113, known in the art as a frame buffer for storing image data arrays, and a serial interface module that links the computer system 107 through a high speed serial link 115 to a system control 122.

The system control 122 includes a series of modules which are connected together by a common backplane 118. The backplane 118 is comprised of a number of bus structures, including a bus structure which is controlled by a CPU module 119. A pulse generator module 121 connects the backplane 118 to the operator console 100 through a serial link 125. It is through this link 125 that the system control 122 receives commands from the operator which indicate the scan sequence that is to be performed.

The pulse generator module 121 operates the system components to carry out the desired scan sequence. It produces data which indicates the timing, strength and shape of the RF pulses which are to be produced, and the timing of and length of the data acquisition window. The pulse generator module 121 also connects to a set of gradient amplifiers 127, and it conveys data thereto which indicates the timing and shape of the gradient pulses that are to be produced during the scan. The pulse generator module 121 also receives patient data from a physiological acquisition controller 129. The physiological acquisition control 129 can receive a signal from a number of different sensors connected to the patient. For example, it may receive ECG signals from electrodes or respiratory signals from a bellows and produce pulses for the pulse generator module 121 that synchronizes the scan with the patient's cardiac cycle or respiratory cycle. And finally, the pulse generator module 121 connects to scan room interface circuit 133 which receives signals from various sensors associated with the position and condition of the patient and the magnet system. It is also through the scan room interface circuit 133 that a patient positioning system 134 receives commands which move the patient cradle and transport the patient to the desired position for the scan.

The gradient waveforms produced by the pulse generator module 121 are applied to a gradient amplifier system 127 comprised of $G_x$, $G_y$ and $G_z$ amplifiers. Each amplifier is utilized to excite a corresponding gradient coil in an assembly generally designated 139. The gradient coil assembly 139 forms part of a magnet assembly which includes a polarizing magnet 140 that produces a 1.5 Tesla polarizing field that extends horizontally through a bore. The gradient coils 139 encircle the bore, and when energized, they generate magnetic fields. In the same direction as the main polarizing magnetic field, but with gradients $G_x$, $G_y$ and $G_z$ directed in the orthogonal x-, y- and z-axis directions of a Cartesian coordinate system. That is, if the magnetic field generated by the main magnet 140 is directed in the z direction and is termed $B_O$, and the total magnetic field in the z direction is referred to as $B_z$, then $G_x=\partial B_z/\partial x$, $G_y=\partial B_z/\partial y$ and $G_z=\partial B_z/\partial z$, and the magnetic field at any point (x,y,z) in the bore of the magnet assembly 141 is given by $B(x,y,z)=B_O+G_x x+G_y y G_z z$. The gradient magnetic fields are utilized to encode spatial information into the NMR signals emanating from the patient being scanned. Because the gradient fields are switched at a very high speed when an EPI sequence is used to practice the preferred embodiment of the invention, local gradient coils are employed in place of the whole-body gradient coils 139. These local gradient coils are designed for the head and are in close proximity thereto. This enables the inductance of the local gradient coils to be reduced and the gradient switching rates increased as required for the EPI pulse sequence. For a description of these local gradient coils which is incorporated herein by reference, see U.S. Pat. No. 5,372,137 issued on Dec. 13, 1994 and entitled "NMR Local Coil For Brain Imaging".

Located within the bore is a circular cylindrical whole-body RF coil 152. This coil 152 produces a circularly polarized RF field in response to RF pulses provided by a transceiver module 150 in the system control cabinet 122. These pulses are amplified by an RF amplifier 151 and coupled to the RF coil 152 by a transmit/receive switch 154 which forms an integral part of the RF coil assembly. Waveforms and control signals are provided by the pulse generator module 121 and utilized by the transceiver module 150 for RF carrier modulation and mode control. The resulting NMR signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150.

The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate local RF head coil to be used in the transmit and receive mode to improve the signal-to-noise ratio of the received NMR signals. With currently available NMR systems such a local RF coil is necessary in order to detect the small variations in NMR signal produced by brain functions.

The NMR signals picked up by the RF coil are digitized by the transceiver module 150 and transferred to a memory module 160 which is also part of the system control 122. When the scan is completed and an entire array of data has been acquired in the memory modules 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the video display 104 as will be described in more detail hereinafter.

Figure 2:
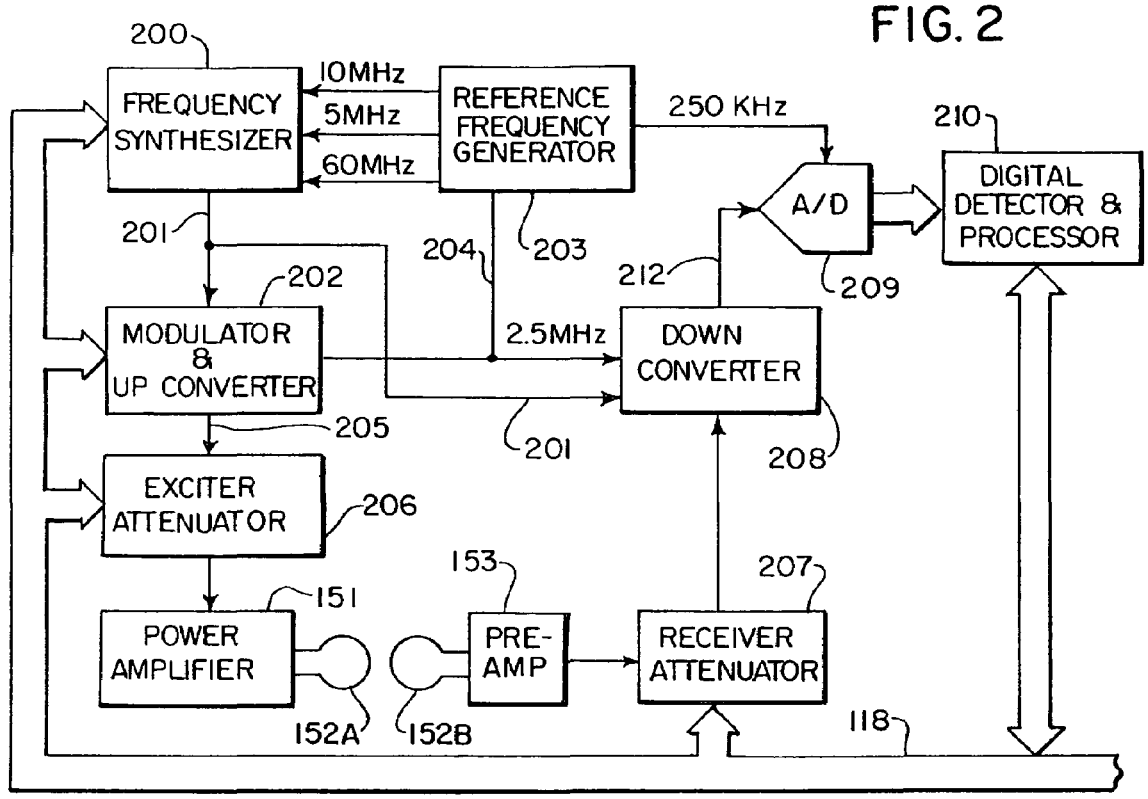
FIG. 2 is an electrical block diagram of a transceiver which forms part of the MRI system of FIG. 1.

Referring particularly to FIGS. 1 and 2, the transceiver 150 includes components which produce the RF excitation field $B_1$ through power amplifier 151 at a coil 152A and components which receive the resulting NMR signal induced in a coil 152B. As indicated above, the coils 152A and B may be a single whole-body coil, but the best results are achieved with a single local RF coil specially designed for the head. The base, or carrier, frequency of the RF excitation field is produced under control of a frequency synthesizer 200 which receives a set of digital signals (CF) through the backplane 118 from the CPU module 119 and pulse generator module 121. These digital signals indicate the frequency and phase of the RF carrier signal which is produced at an output 201. The commanded RF carrier is applied to a modulator and up converter 202 where its amplitude is modulated in response to a signal R(t) also received through the backplane 118 from the pulse generator module 121. The signal R(t) defines the envelope, and therefore the bandwidth, of the RF excitation pulse to be produced. It is produced in the module 121 by sequentially reading out a series of stored digital values that represent the; desired envelope. These stored digital values may, in turn, be changed from the operator console 100 to enable any desired RF pulse envelope to be produced. The modulator and up converter 202 produces an RF pulse at the desired Larmor frequency at an output 205. The magnitude of the RF excitation pulse output through line 205 is attenuated by an exciter attenuator circuit 206 which receives a digital command, TA, from the backplane 118. The attenuated RF excitation pulses are applied to the power amplifier 151 that drives the RF coil 152A. For a more detailed description of this portion of the transceiver 122, reference is made to U.S. Pat. No. 4,952,877 which is incorporated herein by reference.

Referring still to FIGS. 1 and 2 the NMR signal produced by the subject is picked up by the receiver coil 152B and applied through the preamplifier 153 to the input of a receiver attenuator 207. In the preferred embodiment a local receive coil is used. It forms part of the coil assembly described in the above-cited U.S. Pat. No. 5,372,137. The receiver attenuator 207 further amplifies the NMR signal and this is attenuated by an amount determined by a digital attenuation signal (RA) received from the backplane 118. The receive attenuator 207 is also turned on and off by a signal from the pulse generator module 121 such that it is not overloaded during RF excitation. The received NMR signal is at or around the Larmor frequency, which in the preferred embodiment is around 63.86 MHz for 1.5 Tesla. This high frequency signal is down converted in a two step process by a down converter 208 which first mixes the NMR signal with the carrier signal on line 201 and then mixes the resulting difference signal with the 2.5 MHz reference signal on line 204. The resulting down converted NMR signal on line 212 has a maximum bandwidth of 125 kHz and it is centered at a frequency of 187.5 kHz. The down converted NMR signal is applied to the input of an analog-to-digital (A/D) converter 209 which samples and digitizes the analog signal at a rate of 250 kHz. The output of the A/D converter 209 is applied to a digital detector and signal processor 210 which produce 16-bit in-phase (I) values and 16-bit quadrature (Q) values corresponding to the received digital signal. The resulting stream of digitized I and Q values of the received NMR signal is output through backplane 118 to the memory module 160 where they are employed to reconstruct an image.

To preserve the phase information contained in the received NMR signal, both the modulator and up converter 202 in the exciter section and the down converter 208 in the receiver section are operated with common signals. More particularly, the carrier signal at the output 201 of the frequency synthesizer 200 and the 2.5 MHz reference signal at the output 204 of the reference frequency generator 203 are employed in both frequency conversion processes. Phase consistency is thus maintained and phase changes in the detected NMR signal accurately indicate phase changes produced by the excited spins. The 2.5 MHz reference signal as well as 5, 10 and 60 MHz reference signals are produced by the reference frequency generator 203 from a common 20 MHz master clock signal. The latter three reference signals are employed by the frequency synthesizer 200 to produce the carrier signal on output 201. For a more detailed description of the receiver, reference is made to U.S. Pat. No. 4,992,736 which is incorporated herein by reference.

Figure 3:
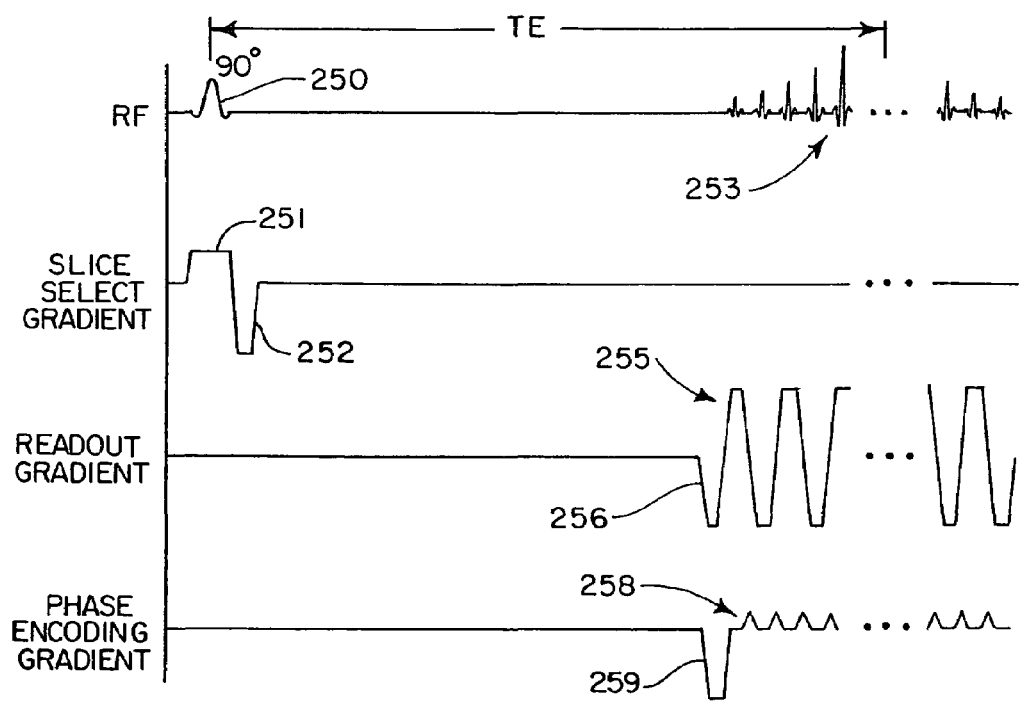
FIG. 3 is a graphic illustration of a preferred pulse sequence employed by the MRI system of FIG. 1 to acquire fMRI images.

The EPI pulse sequence employed in the preferred embodiment of the invention is illustrated in FIG. 3. A 90° RF excitation pulse 250 is applied in the presence of a $G_z$ slice select gradient pulse 251 to produce transverse magnetization in a slice through the brain ranging from 4 to 8 mm thick. The excited spins are rephased by a negative lobe 252 on the slice select gradient $G_z$ and then a time interval elapses before the readout sequence begins. A total of 64 separate NMR echo signals, indicated generally at 253, are acquired during the EPI pulse sequence. Each NMR echo signal 253 is a different view which is separately phase encoded to scan $k_y$-space from $k_y=-32$ to $k_y=+32$ in monotonic order. The readout sequence is positioned such that the view acquired at $k_y=0$ occurs at the desired echo time (TE). In the preferred embodiment an EPI pulse sequence with TE=40 ms and TR=2 sec. is used. From 10 to 12 slices having an in-plane resolution of 3.75 mm, a field of view of 24 cm and a slice thickness of 8 mm are acquired.

The NMR echo signals 253 are gradient recalled echo's produced by the application of an oscillating $G_x$ readout gradient field 255. The readout sequence is started with a negative readout gradient lobe 256 and the echo signals 253 are produced as the readout gradient oscillates between positive and negative values. A total of 64 samples are taken of each NMR echo signal 253 during each 512 microsecond readout gradient pulse 255. The successive 64 NMR echo signals 253 are separately phase encoded by a series of $G_y$ phase encoding gradient pulses 258. The first pulse is a negative lobe 259 that occurs before the echo signals are acquired to encode the first view at $k_y=-32$. Subsequent phase encoding pulses 258 occur as the readout gradient pulses 255 switch polarity, and they step the phase encoding monotonically upward through $k_y$ space.

At the completion of the EPI pulse sequence, therefore, 64 separate frequency encoded samples of 64 separately phase encoded NMR echo signals 253 have been acquired. This 64×64 element array of complex numbers is Fourier transformed along both of its dimensions ($k_y$ and $k_x$) to produce a 64×64 element array of image data that indicates the NMR signal magnitude along each of its two dimensions (y and x). The 10 to 12 slices are positioned such that NMR data is acquired from the entire region of the subject's brain that is of interest.

In order to suppress the signal from cerebral spinal fluid, the EPI pulse sequence may be preceded by an inversion recovery preparation pulse sequence. As is well known in the art, inversion recovery pulse sequences include a 180° rf excitation pulse that inverts the longitudinal spin magnetization, followed by a recovery period TI in which the longitudinal magnetization of the desired spin species recovers, but that of undesired spin species does not. In the preferred embodiment TI is set to 750 milliseconds to suppress the longitudinal magnetization of cerebral spinal fluid spins prior to performing each EPI pulse sequence.

Functional magnetic resonance imaging (fMRI) has been used extensively to study normal brain function, psychiatric conditions, learning disabilities, neurodegenerative conditions, recovery from stroke, and the relationship of eloquent cortex to brain tumors and arteriovenous malformations (AVMs). The pre-operative use of fMRI to identify eloquent cortex near resectable lesions is becoming a common clinical imaging scenario. Mapping eloquent cortex with fMRI relies on blood oxygen level dependent (BOLD) contrast.

The physiological basis of BOLD signal is the regional vasoactive response induced by neuronal activity, causing increases in regional cerebral blood flow (rCBF), blood oxygen concentration, and consequently, fMRI signal. Yet, it is clear that the BOLD contrast mechanism can be significantly compromised adjacent to regional cerebral pathology. For example, cortical BOLD signal can be reduced by the presence of glial tumors, both at the edge of the tumor and in vascular territories somewhat removed from the tumor. Loss of regional cerebral vasoactivity near lesions is thought to be a major contributing factor in the loss of cortical BOLD signal. Such uncoupling of the BOLD signal resulting from the loss of vasoactivity and neuronal activity within the same regions can result in the underestimation of genuine neuronal function and may alter the diagnostic accuracy of BOLD fMRI.

Figure 4:
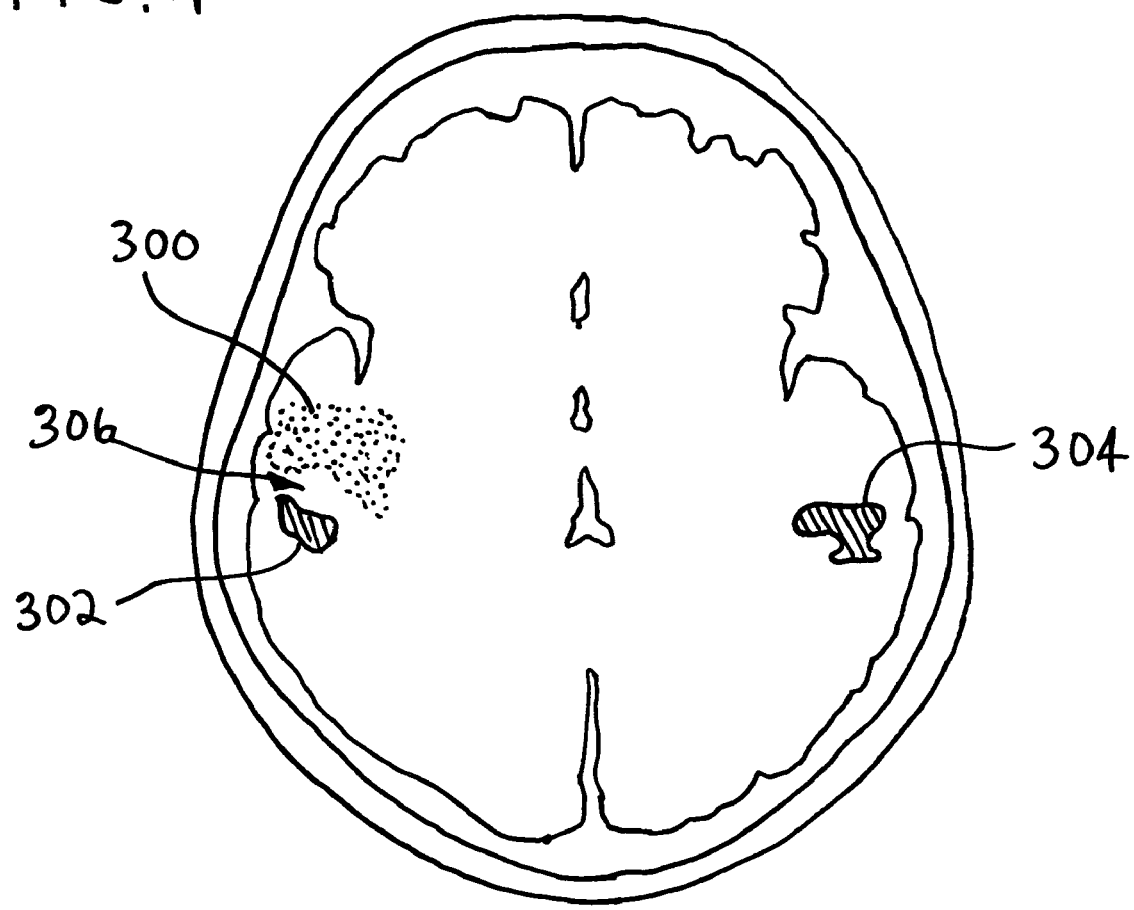
FIG. 4 is a pictorial representation of an anatomic MR image of a subject's brain with acquired fMRI activation regions superimposed thereon.

Referring to FIG. 4 for example, an MR image of the brain of a subject may indicate a tumor at 300. Subsequent fMRI testing may reveal neuronal activity in response to a particular stimulus at regions 302 and 304. Based on the fMRI data, the surgeon might reasonably conclude that the tumor 300 can be removed with little risk of impairing the subject's response to this particular stimulus. What we have discovered, however, it that in limited number of cases such as this, what appears to be a buffer zone 306 between the tumor 300 and the region of measured neuronal activity 302 is in fact neuronally active and cannot be removed with the tumor 300 without significantly impairing the subject.

Lesion-induced neurovascular uncoupling may have particularly profound consequences in the pre-operative assessment of resectable lesions, where the functional demands of a task cause bilateral hemispheric activation, such as speech and language, motor, supplementary motor, and higher cognitive functions. It is common to assume that a greater extent and/or magnitude of cortical activation in one hemisphere of the brain are indicative of functional dominance in that hemisphere. Based on that assessment more aggressive surgery may be performed in the same region of the other hemisphere without significantly impairing the subject. If, under pathological conditions, normal or near normal function is maintained but fMRI shows a shift in relative hemispheric activation away from the hemisphere containing a lesion, then it might be assumed that the function of the affected cortex has been taken over by the homologous area in the unimpaired brain hemisphere. Indeed, fMRI data showing a lesion-induced shift in relative hemispheric activation have been taken as evidence for cortical reorganization. However, this premise can be erroneous if, under certain conditions, the BOLD mechanism rather than neuronal function is selectively impaired, particularly if there are increased demands placed on homologous brain regions.

Figure 5:
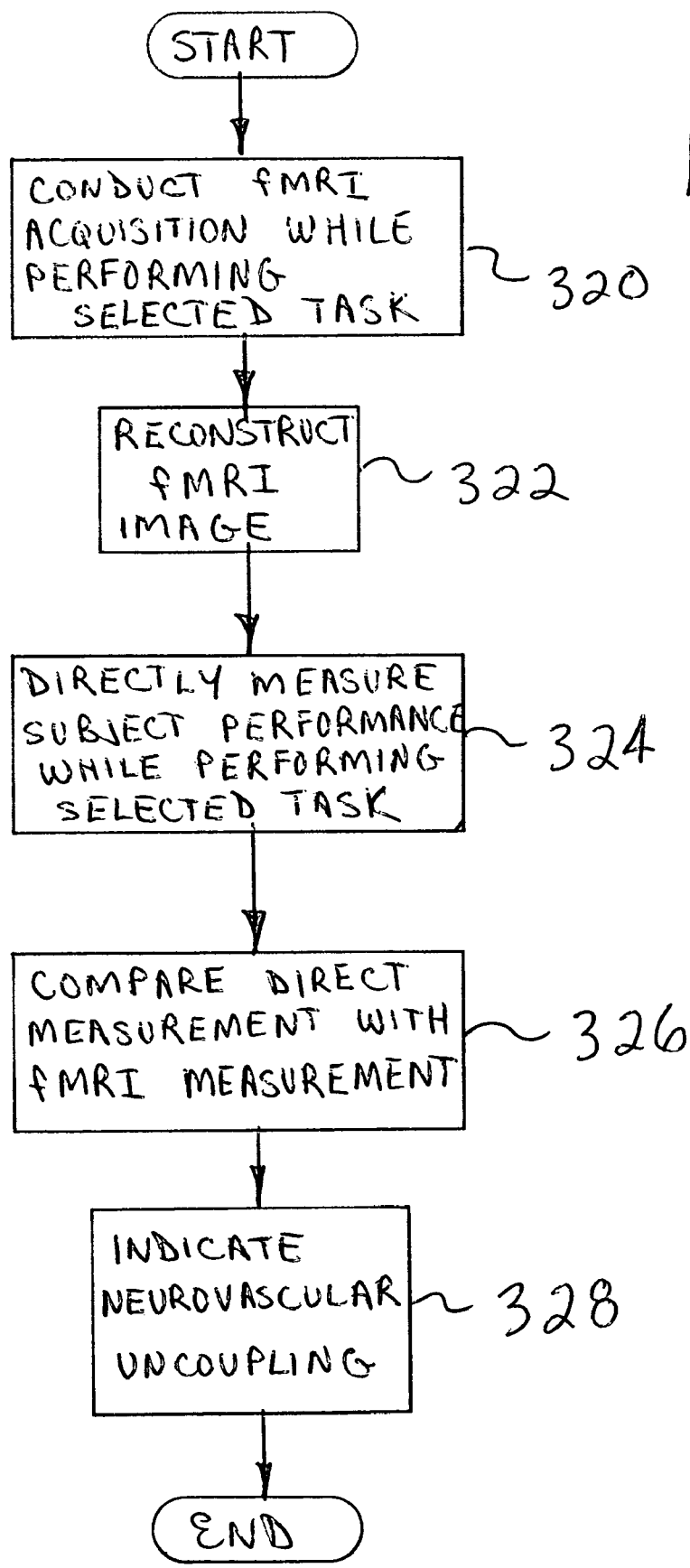
FIG. 5 is a flow chart indicating the steps performed when practicing the preferred embodiments of the invention.

Referring particularly to FIG. 5, a method for measuring neurovascular uncoupling that can lead to such erroneous conclusions adds a number of steps to the basic fMRI process. As indicated at process block 320 an fMRI acquisition is conducted using the above EPI pulse sequence while the subject performs a selected task. As will be explained in more detail below, the EPI pulse sequence described above is typically repeated 100 times for each slice to acquire time course NMR data for 100 images. As explained above, a two dimensional Fourier transformation is performed by the array processor 161 and the resulting NMR image data set is processed as described in U.S. Pat. No. 5,603,322 to produce an fMRI image as indicated at process block 322. Referring to FIG. 4, for example, typically an anatomic image is also obtained and reconstructed with the regions of fMRI activity 302 and 304 superimposed on it.

The next step as indicated by process block 324 is to directly measure the subject's performance of the selected task. As will be described in more detail below, the measurement made will depend on the particular task being performed. For example, if the somato sensory regions of the brain are at risk the sense of touch at landmark locations on the body are tested. If the visual cortex is at risk, the subject's entire field of view is measured using a perimetry test. Motor skills can also be tested directly, as can speech and language skills. In other words, a non-fMRI measurement of the selected task is carried out.

As indicated at process block 326, the results of the fMRI measurement is then compared with the results of the non-fMRI measurements. As will be described in more detail below, the manner in which the comparison is done will depend on the particular task being measured, but in any case the result is an indication of any differences between the neuronal activity as measured by fMRI and neuronal activity as determined by the direct measurement. The existence of any difference is in itself an indication of neurovascular uncoupling that may render the fMRI data unreliable for surgical planning. While the existence of neurovascular uncoupling can be simply indicated at process block 328, in the preferred embodiments of the invention the detected uncoupling is localized to particular regions in the subject's brain. Referring again to FIG. 4, if the neurovascular uncoupling is occurring in the region 306, for example, this is indicated by changing the color of the image pixels in locations where the uncoupling is detected. Such uncoupling in this example indicates to the surgeon that removal of tumor 300 may have a deleterious impact on the subject and most certainly indicates that the tumor should be carefully resected in this region 306.

Indicating Visual Cortex Neurovascular Uncoupling

Figure 6:
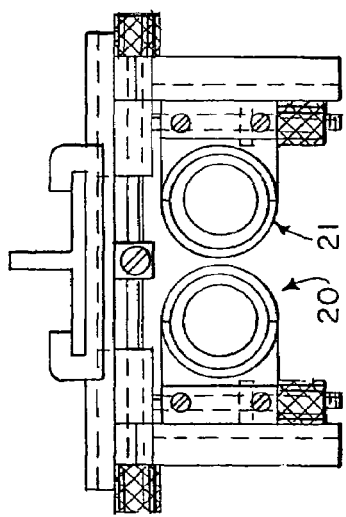
FIGS. 6 and 7 are side and end elevation views of a patient video system used to practice one embodiment of the invention.
Figure 7:
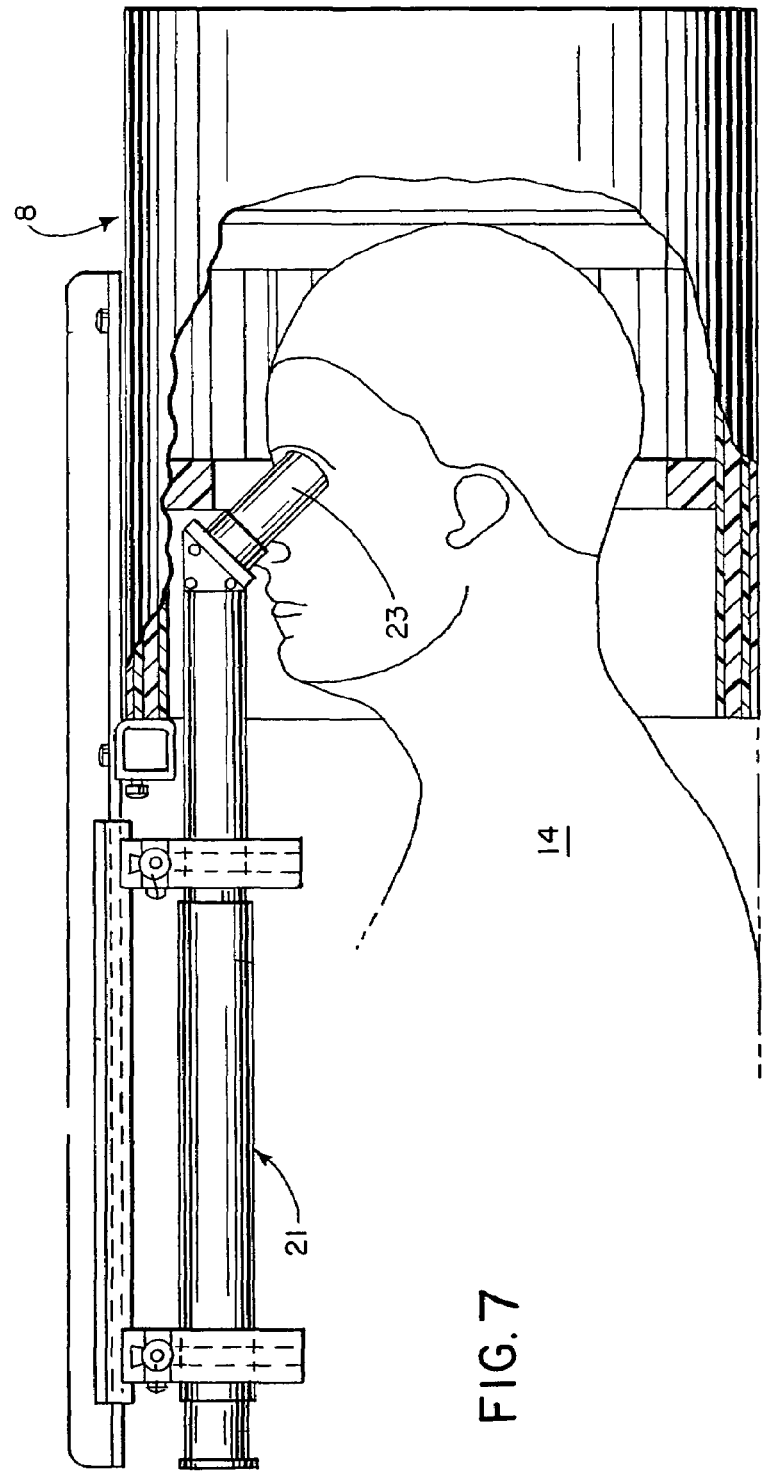

To practice this embodiment of the present invention it is necessary to provide visual stimulation to the subject during the performance of the fMRI scan. This is achieved using the patient video system described in U.S. Pat. No. 5,339,813 which is incorporated herein by reference. Referring particularly to FIGS. 6 and 7, this patient video system includes a pair of scopes 20 and 21 which are mounted to the local coil assembly 8 and positioned with their eyepieces 23 against the eyes of the patient 14. The scopes 20 and 21 are aimed along the bore axis 13 at a target area located remotely from the magnet assembly. The scopes 20 and 21 pass between the patient's face and the closely surrounding head coil 8 and they extend a substantial distance.

A display system is positioned in the target area of the scopes 20 and 21. This location is at least sixteen feet from the magnet assembly so that conventional electronic and optical technologies can be employed without damage or image distortion from the high magnetic fields. A model XG-2000 u LCD video projector commercially available from Sharp Corporation, Osaka, Japan has been modified for this purpose. The display system produces a 2"×2" color image at a front opening in response to a conventional RGB video signal received from a computer. The computer receives the image data from disc storage or it may be computed in real-time, and in brain function experiments, a sequence of images may be played out in a repetitive pattern. The two inch square image produced by the display is magnified by the scopes 20 and 21 to form an image which fills the patient's field of view.

As described in U.S. Pat. No. 6,430,431 which is incorporated herein by reference, a pattern is produced on the display system which tests the subject's vision throughout his or her entire visual field.

To map angular positions within the visual field, subjects viewed a flickering, black and while checkered hemifield (mean luminance approx. 20 cd/m$^2$) that rotates slowly (one revolution every 40 seconds) about a central fixation point during the fMRI scan. To map visual field eccentricity (distance from the center of gaze), subjects viewed an expanding checkered annulus. In this manner, neurons responding to stimulation at different locations in the visual field were activated at different times during the stimulus sequence. Corresponding differences in the temporal phase of the fMRI response thus identified the retinotopic location yielding a maximal response for each active site in the brain.

While the stimulation pattern is produced a series of images are acquired using the above described EPI pulse sequence. These images are formed into a 3D array of data in which one dimension is time. The fMRI response of an image voxel is a time course voxel vector that indicates the change in amplitude and phase of the NMR signal at that voxel over the time of the study. Cortical sites of significant activation in the subject's brain were identified by cross-correlating the response NMR signal waveform for each time course voxel vector with a reference voxel vector in the form of a sine function that closely approximates the ideal response to the visual stimulus smoothed and delayed by the cortical hemodynamics. Under the null hypothesis (no signal present), the cross-correlation coefficient follows the incomplete beta distribution, thereby permitting calculation of the statistical significance, p, based on 96 degrees of freedom in the MR time series (100 minus 4 fit coefficients for the phase and amplitude of the reference waveform). In this embodiment, voxels were considered active if they each passed a threshold of $p<=6.2\times10^{-8}$, (corresponding to $r>=0.54$ for 96 degrees of freedom). Using a Bonferroni correction for multiple comparisons this is equivalent to $p<=0.003$ for the entire brain volume.

In order to reconstruct brain activation maps from the acquired fMRI data, all voxels exceeding the criterion are displayed with the color of each voxel representing the amplitude of the best-fit reference waveform. The resultant functional images are combined with anatomical images and assembled into a combined 3-dimensional, volumetric data set that can be displayed. In this manner, the visual stimulation of each location in the subject's field of view may be associated with specific locations/voxels in the visual cortex that are activated.

In order to compare the fMRI measurements with direct measurements of the subject's vision, the fMRI mapping data are converted into a functional field map that permits direct visualization of the pattern of blindness within the subject's field of view. The retinotopic mapping measurements described above identified optimal visual field eccentricity (expanding ring) and polar angle (rotating hemifield) for activating individual voxels in the subject's visual cortex. For each responsive voxel, the annulus and hemifield mapping measurements yield the polar coordinates of the visual field position that, when stimulated in the prescribed pattern, induce the maximum response. To create the functional field map, a symbol is placed at the corresponding coordinates on a diagram of the subject's visual field. The amplitude of the fMRI response for that voxel is indicated by symbol color. The size of the symbol is scaled according to the estimated 90% confidence zone for the true location of the data point. This procedure is repeated for all responsive voxels or for selected subsets of voxels as desired to produce the fMRI functional field map indicated in FIG. 8A. Note, that in a fully sighted individual there will be symbols on the functional field map for all locations in the field of view. For patients having localized areas of blindness, there will be few, or no, voxels at the corresponding visual field locations or their amplitudes will be very low.

The direct measurement of the subject's visual field is made next using a special computerized instrument for performing automated perimetry. Instruments, such as those described in U.S. Pat. Nos. 5,459,536 and 6,527,391 measure the limit or threshold of a subject's perception of light at an array of test locations in the subject's visual field.

Typically, the test is performed in the following way. The subject is seated in front of a perimeter and asked to look steadily at a centrally placed fixation target, e.g. on a screen or in a hemispherical bowl. Visual stimuli are presented successively with different intensities and at different locations on the screen. The patient is asked to press a response button every time he perceives a stimulus, whether close to or distant from the fixation target, whether faint or strong. Alternatively or additionally, the perception of stimuli can be recorded by objective methods, such as measurement of electric potentials in the brain or in the eye of the patient (VER perimetry and ERG perimetry, respectively) or recording of pupil reactions (pupil perimetry).

There are different strategies for selecting test locations and intensities of the stimuli presented at these test locations in order to establish a patient's threshold for perception of light. In one common method, the so-called staircase method, a stimulus which has an intensity close to the expected threshold value at the test location concerned is shown. If the patient does not respond to the stimulus, the intensity of the subsequently presented stimuli is thereafter increased stepwise until a response is received from the patient, i.e. until a stimulus is seen. The first intensity level at which a response is received may be defined as an estimate of the threshold of the test location concerned. As shown in FIG. 8B, this directly measured vision information is typically displayed as an array of pixels in which the visual response is indicated by color. If a particular location is not responsive at any threshold, a value of "zero" is displayed.

Figure 8A:
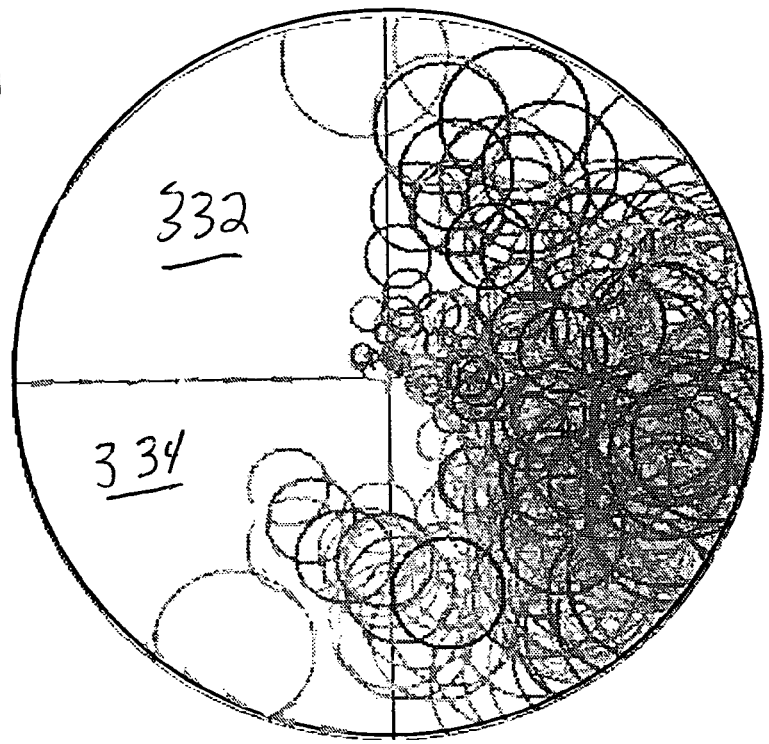
FIG. 8A is a functional field map produced using a preferred embodiment of the invention.
Figure 8B:
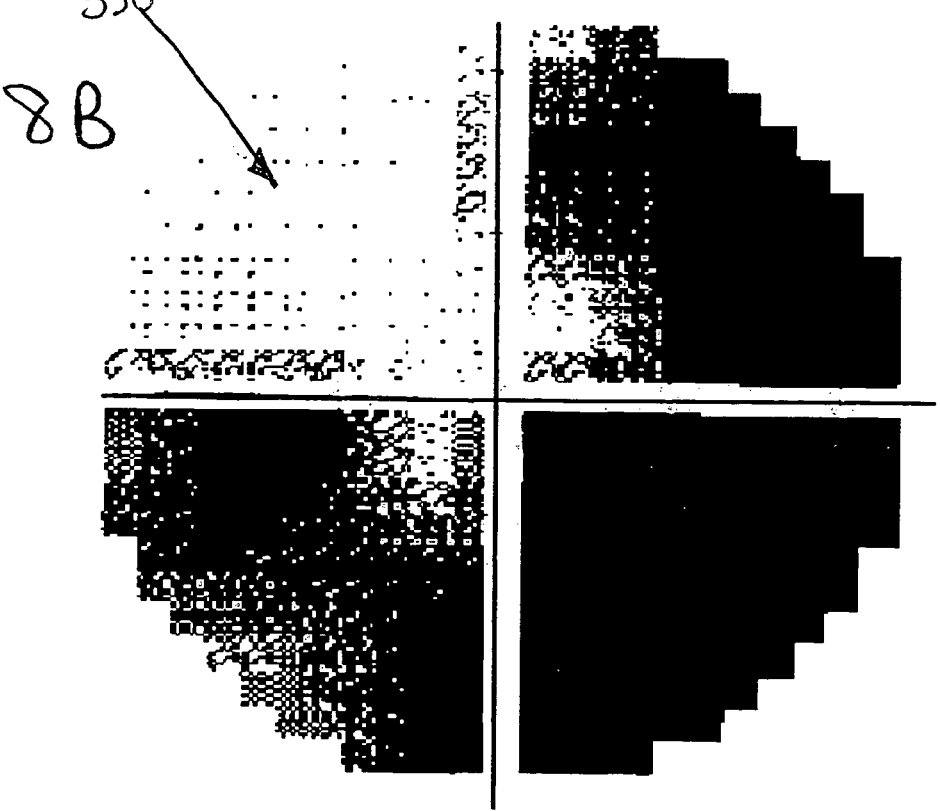
FIG. 8B is a visual field map used with the functional field map of FIG. 8A to practice a preferred embodiment of the invention.

The next step in the process is to compare the fMRI functional field map of FIG. 8A with the directly measured visual field of FIG. 8B. If the locations in the fMRI functional field map where there is little or no signal amplitude correspond exactly with locations in the measured visual field where the threshold value is very high or zero, there is no neurovascular uncoupling and the fMRI data can be used for surgical planning. On the other hand, if locations in the measured visual field indicate viable neuronal activity but the same locations in the fMRI functional field map indicate little or no viability, then neurovascular uncoupling is indicated. In the example depicted in FIGS. 8A and 8B the direct measurement visual field of FIG. 8B indicates loss of vision in the upper-left quadrant 330. The fMRI functional field map of FIG. 8A, on the other hand, indicates the loss of vision not only in the upper left quadrant 332, but also in the region 334 in the lower left quadrant. The difference region 334 thus indicates a corresponding region in the brain where neurovascular uncoupling is occurring.

Automated detection of neurovascular uncoupling: First, the functional field map and the directly measured perimetry map are constructed, superimposed and examined for zones of mismatch indicative of neurovascular uncoupling. For automated detection, we use the "R" analysis package and "kriging" (a generalized method for 2-dimensional interpolation/smoothing) to regrid the functional field map and directly measured perimetry data onto identical, regular grids of data points. Data from corresponding points on each regirdded map is then subjected to a binary thresholding procedure and subsequent logical comparison to identify zones of neurovascular uncoupling mismatch.

While the detection of neurovascular uncoupling alone is very useful, a further step is employed to indicate the locations in the anatomical image of the brain where the uncoupling is occurring. In all cases of neurovascular uncoupling identified so far, only a restricted portion of the visual field is involved. Data in the remainder of the field remains valid. This suggests a potential compensatory strategy whereby the retinotopic organization of the "missing" zone of fMRI activation is extrapolated from intact portions of the cortical visual field map. This can be accomplished through a modification of a technique described by Dougherty et al. Briefly, an automated computer algorithm is used to optimally fit a standardized "normative grid" of the cortical visual field map to the existing fMRI data. The configuration of the portion of the template corresponding to the missing fMRI data is adjusted to smoothly fit the data at the margins of the affected zone. Once the template is optimally fit to the intact data, the retinotopy of the neurovascular uncoupling zone can be estimated and marked on both the brain map and the functional field map thereby allowing diagnosis and treatment planning to proceed, but with clear indication of neurovascular uncoupling areas where caution should be observed.

These neurovascular uncoupled locations are indicated by changing the pixels to a selected color that distinguishes them from the colors used to display the fMRI activity on the anatomical image. Referring again to FIG. 4, for example, such uncoupling would be indicated by changes in color of the pixels located in the region 306.

Indicating Sensory-Motor Cortex Neurovascular Uncoupling

The somatotopic organization of the sensori-motor homunculus provides the opportunity to map the entire homunculus in a very time efficient manner, because each stimulated body part on a subject activates a specific site in the sensory and motor cortex of the subject's brain. Functional imaging studies using positron emission tomography and fMRI in humans have shown a good correlation of activation within sensori-motor cortex between active and passive movements of the distal upper extremity. Preliminary data in our laboratory has demonstrated good correlation of primary sensori-motor cortical activation elicited by active and passive movements of other body parts as well, indicating that it is feasible to map the entire sensori-motor homunculus utilizing passive sensory stimulation. Passive extremity movements will result in activation of corresponding efferent zones in MI cortex, and that stimulation of those efferent zones will reproduce that same movement. This phenomenon is believed to be due to cortico-cortical connections between primary (SI) and secondary (SII) sensory cortex and MI cortex.

To examine the sensory-motor cortex regions of the brain fMRI data is acquired while passive and active movements are performed and while different locations on the subject's body are touched or otherwise stimulated. The precise movements or stimulations performed in the test will depend on the region in the brain of primary concern. The acquired fMRI data is processed as described above to reconstruct an fMRI image and a functional field map such as that depicted in FIG. 9A is produced. We visualize the cortical brain activation as a topographic projection onto a diagram of the patient's body. The resulting display shows which portions of the patient's body are able to evoke a brain response to stimulation. This functional field map indicates the fMRI response at locations on the subject by circles. The color of the circles indicate fMRI signal amplitude and its diameter indicates certainty of position. In the example shown in FIG. 9A there is no fMRI response indicated for the patient's left forearm and hand indicated generally at 338 and for the lower left leg and foot indicated generally at 339.

To determine the quality of the fMRI data, and to distinguish between zones of neuronal dysfunction and neurovascular uncoupling in the sensori-motor system, passive peripheral stimuli are applied to individual body parts in a sequential, temporal method analogous to visual field mapping. A sensory map indicating the directly measured response of the subject is then produced as shown in FIG. 9B. In this example, the direct measurements of the subject's response indicate a loss of sensitivity to stimuli in the lower left leg which is indicated by a darkened region 340.

The region of neurovascular uncoupling is determined by comparing the sensorimotor functional field map of FIG. 9A with the sensory map of FIG. 9B. When this is done as illustrated by the overlay of the two maps in FIG. 9C, it is readily apparent that the region indicated at 342 in the subject;s left arm is responsive to direct measurements, but not responsive to BOLD fMRI measurements. This region can be mapped to corresponding regions in the brain, and it is these cortical regions that are not responsive to BOLD fMRI measurements due to neurovascular uncoupling.

As with the vision measuring method discussed above, the cortical regions of neurovascular uncoupling detected according to the present invention may be indicated by color coding pixels in the anatomic image of the brain to distinguish from the tumor and the fMRI responsive regions in the brain. This is done by mapping the regions on the subject's body that indicate neurovascular uncoupling to corresponding regions in the brain using a method such as that described by Wilder Penfield et al in "Somatic Motor And Sensory Representation In The Cerebral Cortex Of Man As Studied By Electrical Stimulation", *Brain* 1938; 15:389-443.

The advantages of the sensorimotor functional field map display are directly analogous to the vision functional field map display. It provides a very intuitive way of relating the pattern of brain activation as measured by fMRI to the pattern of sensory perception on the patient's body. Moreover, since the functional field map is calculated directly from the fMRI signals regardless of the physical locations of the voxels, it is unaffected by physical distortions of the brain, as can occur with rapidly growing tumors. These characteristics make the functional field map particularly useful for quality assessments. A perception of the peripheral stimulus by the subject without accompanying fMRI response in the same body part of a functional field map for primary motor and sensory cortex is a spatial indication of the effects of lesion-induced neurovascular uncoupling that is hindering the BOLD signal response. Zones of neurovascular uncoupling are then represented on a diagram of the body, corresponding to specific stimulated body parts. The result is an efficient diagrammatic composite of neurovascular coupling and uncoupling that can be used to assess data quality and to identify specific, under-represented areas of sensori-motor cortical activation in BOLD fMRI procedures.

The invention claimed is:

1. A method for detecting neurovascular uncoupling in the brain of a subject, the steps comprising:
    a) acquiring fMRI data from the subject with a magnetic resonance imaging system that measures brain activity in response to at least one of a selected stimulus applied to the subject and a selected task performed by the subject;
    b) transforming the fMRI data to a first map;
    c) measuring a behavioral response of the subject to the at least one selected stimulus and selected task performed by the subject;
    d) creating a second map based on the measured behavioral response in step c);
    e) comparing the first map created in step b) with the second map created in step d); and
    f) indicating a difference between the first map and the second map as neurovascular uncoupling.

2. The method as recited in claim 1 in which step a) measures the subject's field of vision and step b) includes
    producing a functional field map from the acquired fMRI data that indicates the locations in the subject's visual field that correspond to locations of indicated brain activity.

3. The method as recited in claim 2 in which step c) includes measuring the subject's field of view and step d) includes producing a visual field map that indicates the locations in the subject's visual field which the subject can actually see.

4. The method as recited in claim 1 in which step f) includes:
    f)i) displaying an anatomical image of the subject's brain;
    f)ii) converting the difference regions between the two maps relating to neurovascular uncoupling to corresponding regions in the image of the brain of i); and
    f)iii) displaying on the anatomical image regions where neurovascular uncoupling is indicated.

5. The method as recited in claim 1 which includes:
    g) acquiring MRI data from the subject and reconstructing therefrom an anatomical image of the subject's brain;
    h) displaying regions of brain activity on the anatomical image indicated by the acquired fMRI data; and
    step f) includes displaying regions of neurovascular uncoupling on the anatomical image.

6. The method as recited in claim 1 in which step a) measures the subject's response to at least one of active movement and passive stimulation at a plurality of locations on the subject's body; and step b) includes:
    producing a functional field map from the acquired fMRI data that indicates the locations on the subject's body that correspond to locations of indicated brain activity.

7. The method as recited in claim 6 in which step c) includes measuring the subject's response to the at least one of active movement and the passive stimulation and step d) producing a sensory map that indicates the locations on the subject's body which are responsive.

8. The method as recited in claim 1 in which step b) includes producing a functional field map from the acquired fMRI data that may be used in step e) to compare response of the subject to direct measurements.

9. The method as recited in claim 1 in which step f) includes indicating neurovascular uncoupling when the second map includes data in a portion of the map and the first map has an absence of data in a corresponding portion of the second map.

* * * * *

UNITED STATES PATENT AND TRADEMARK OFFICE
CERTIFICATE OF CORRECTION

| | | |
|---|---|---|
| PATENT NO. | : 7,469,159 B2 | Page 1 of 1 |
| APPLICATION NO. | : 11/138509 | |
| DATED | : December 23, 2008 | |
| INVENTOR(S) | : Edgar Deyoe et al. | |

It is certified that error appears in the above-identified patent and that said Letters Patent is hereby corrected as shown below:

Column 14, claim 7, line 54, "step d)" should be --step d) includes--.

Signed and Sealed this

Seventeenth Day of February, 2009

JOHN DOLL
*Acting Director of the United States Patent and Trademark Office*